United States Patent [19]

Garbe et al.

[11] Patent Number: 4,986,701
[45] Date of Patent: Jan. 22, 1991

[54] PROCESS FOR MANUFACTURING A CYLINDRICAL BODY AND A DEVICE FOR CARRYING OUT THE PROCESS

[75] Inventors: Heyno Garbe, Baden; Dietrich Königstein, Gebenstorf, both of Switzerland

[73] Assignee: ASEA Brown Boveri Ltd., Baden, Switzerland

[21] Appl. No.: 436,744

[22] Filed: Nov. 15, 1989

[30] Foreign Application Priority Data

Nov. 19, 1988 [DE] Fed. Rep. of Germany ....... 3839212

[51] Int. Cl.⁵ .............................................. B23B 35/00
[52] U.S. Cl. .................................. 408/1 R; 73/864.44; 408/80; 408/204; 408/703
[58] Field of Search ..................... 408/1 R, 203.5, 204, 408/703; 73/864.44, 864.45, 72 R, 79, 80

[56] References Cited

U.S. PATENT DOCUMENTS

| | | |
|---|---|---|
| 3,587,560 | 6/1971 | Glassman ......................... 408/204 X |
| 3,700,341 | 10/1972 | Block .................................... 408/1 R |
| 4,131,042 | 12/1978 | Rich et al. ............................ 83/100 |
| 4,452,554 | 6/1984 | Hougen ............................ 408/204 X |
| 4,676,701 | 6/1987 | Palm .................................... 408/67 |
| 4,696,308 | 9/1987 | Meller et al. ..................... 408/204 X |

FOREIGN PATENT DOCUMENTS

| | | |
|---|---|---|
| 70087 | 8/1955 | Fed. Rep. of Germany . |
| 2621687 | 12/1977 | Fed. Rep. of Germany . |
| 8301307.5 | 5/1983 | Fed. Rep. of Germany . |
| 3321091A1 | 12/1984 | Fed. Rep. of Germany . |
| 8521577.5 | 5/1986 | Fed. Rep. of Germany . |
| 3529603C2 | 8/1987 | Fed. Rep. of Germany . |
| 928210 | 11/1947 | France . |
| 122317 | 1/1919 | United Kingdom . |

OTHER PUBLICATIONS

"Circle Cutter is Powered by Hand", American Machinist, Mar. 25, 1957, p. 134.

*Primary Examiner*—Steven C. Bishop
*Attorney, Agent, or Firm*—Burns, Doane, Swecker & Mathis

[57] ABSTRACT

A process for manufacturing a cylindrical body and a device for carrying out the process.

With this process, in particular sample bodies of absorbents are obtained.

The intention with this process is that the nature of the bodies taken is not falsified. A device, which allows this process to be carried out rationally, is to be specified. This is achieved by the fact that firstly a plane-parallel board (1) is cut out of the material, which board (1) is provided with a guide opening (4a). Inserted into the guide opening (4a) is a guide part (5) which guides a cutting element (9) concentrically to the said guide opening (4a), which cutting element (9) separates a sleeve-shaped body (13). This body (13) is then introduced into a measurement device.

8 Claims, 1 Drawing Sheet

PROCESS FOR MANUFACTURING A CYLINDRICAL BODY AND A DEVICE FOR CARRYING OUT THE PROCESS

BACKGROUND OF THE INVENTION

1. Field of the invention

The invention relates to a process for manufacturing a cylindrical body made of a comparatively easily deformable material, in particular made of an absorbent, and to a device for carrying out this process.

2. Discussion of Background

Taking material samples from absorbents is difficult since this material generally has a sponge-like structure and can only be subjected to comparatively low mechanical stresses. When taking samples, e.g. by punching, the material of the samples is frequently deformed and compressed as a result of the mechanical stress. If samples are obtained with the aid of machining procedures, shavings frequently penetrate the material of the sample and falsify its density. The electrical characteristics of samples obtained in this manner deviate from those of the starting material.

Here the invention can provide a solution. The invention, as characterized in the claims, achieves the object of specifying a process for manufacturing a cylindrical body from a comparatively easily deformable material, in particular from absorbents, with which process the nature of the body is not falsified, and of showing a device, with the aid of which the process can be carried out rationally.

SUMMARY OF THE INVENTION

Accordingly, the advantages achieved by the invention are to be seen essentially in the fact that representative sample bodies can be taken even from comparatively soft materials of sponge-like design, without the structure of the bodies being stressed impermissibly during manufacture and without their density being falsified. There is a further advantageous effect in that these bodies can be manufactured with such precision that they exactly fill the hollow space of a measurement apparatus set up coaxially such that very precise measurements can be performed on them.

The further embodiments of the invention are the subject of the dependent claims.

BRIEF DESCRIPTION OF THE DRAWINGS

A more complete appreciation of the invention and many of the attendant advantages thereof will be readily obtained as the same becomes better understood with reference to the following detailed description when considered in connection with the accompanying drawings, wherein.

DESCRIPTION OF THE PREFERRED EMBODIMENTS

Figure 1:
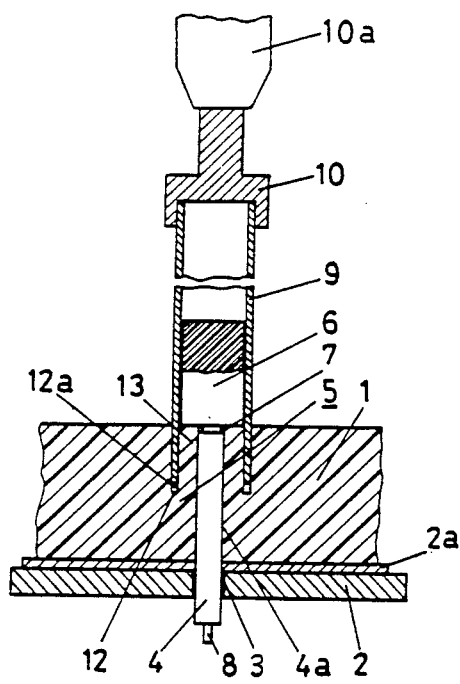
FIG. 1 shows a first embodiment of the device according to the invention.

Referring now to the drawings, wherein like reference numerals designate identical or corresponding parts in all figures.

FIG. 1 shows a device according to the invention for manufacturing cylindrical sample bodies from absorbents. A piece of a plane-parallel board 1 of absorbent, which was manufactured, for example, by means of a circular saw or a band saw, lies on a support 2. This support 2 can be considered as part of a boring machine 10a. The support 2 has a bore-hole 3, which is penetrated by a cylindrical shaft 4 of a guide part 5. At the same time, the shaft 4 penetrates a guide opening 4a, which extends perpendicular to the surface of the board 1 and positions this board 1. The guide part 5 consists of the shaft 4 and a head part 6, which has a larger diameter than the shaft 4. The guide part 5 can be designed in one piece or several pieces. The head part 6 has a shoulder 7 which is supported on the board 1. At the bottom, the shaft 4 has a threaded bolt 8. The head part 6 extends upwards in the axial direction, the axial extent being at least 1.5 times its diameter, such that good guidance of a cutting element 9, of tubular design, is guaranteed, the cutting element 9 enclosing the guide part 5 concentrically. The cutting element 9 is held in a mount 10 which is in effective connection with the boring machine. An arrow 11 indicates that the cutting element 9, together with the mount 10 can be moved downwards in the axial direction by an adjustable forward feed. In this case, the cutting element 9 rotates at the same time and acts on the board 1 with its end face 12, which is provided with teeth 12a, and cuts a body 13, of sleeve-shaped design, from the material of the board 1.

Figure 2:
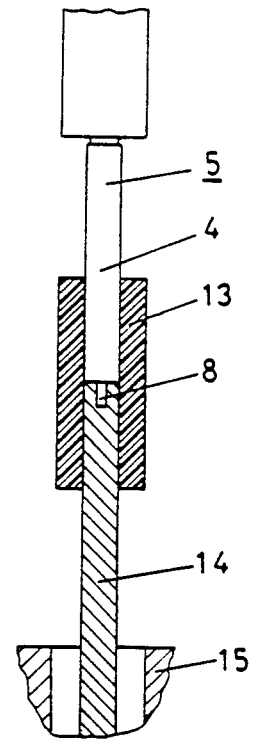
FIG. 2 shows a sketch of the sample body being taken.

On removal of the cutting element 9, the body 13 is taken out together with the guide part 5. As shown in FIG. 2, a slideway 14, of cylindrical design, is then screwed onto the threaded bolt 8 and connected without jolting to the guide part 5. The body 13 is then pushed onto the slideway 14 by the shaft 4 of the guide part 5 and, after releasing the screw connection, the body 13 carried by the slideway 14 is introduced into a measurement device. The slideway 14 is an integral part of this measurement device.

The head part 6 of the guide part 5 serves as a guide for the cutting element 9 surrounding it. The material matching here must be selected in such a way that no abrasion products can arise which fall down and can falsify the material of the sample body. The cutting element 9 is preferably produced from hardened steel, the head part 6, in contrast, preferably of softer material. The head part 6 can be produced from softer metal such as, for example, unhardened types of steel, brass or bronze, but it can also consist of plastic, in particular polytetrafluoracthylene (TEFLON). The entire guide part 5 can be produced in one piece from the respective material, but it can also be composed of different materials. However, it would also suffice if the head part 6 of the guide part 5 were coated, for example with TEFLON, in the region in which it guides. Furthermore, it is expedient to grind the cutting teeth 12a on the end face 12 of the cutting element 9 in such a way that eroded particles of material from them are removed in the radial direction towards the outside. In this way, these particles of material are prevented from becoming deposited on the body 13 and falsifying its density or structure.

The boring machine 10a has an adjustable rate of forward feed as a homogeneous surface of the sample body is achieved by an even cutting rate. Rates of forward feed in the range of 5 mm per second to 0.1 mm per second have proved to be advantageous. With board thicknesses of about 10 cm, sample bodies can thus be taken in a rational and reliable manner.

Furthermore, it proves to be expedient to insert an intermediate layer 2a between the board 1 and the support 2, if this is produced for example from steel, in order to save the end face 12 of the cutting element 9 from wear. The intermediate layer 2a is therefore advantageously produced from a soft material, which is nevertheless stable in shape, such as for example rubber.

With the process for manufacturing cylindrical sample bodies, in particular from absorbents, a plane-parallel board 1 of the respective material is firstly cut out. Using a twist drill, a guide opening 4a is then drilled into this board 1, perpendicular to the plane-parallel surfaces. The shaft 4 of a guide part 5, of cylindrical design, is introduced, fitting exactly, into this guide opening 4a. The guide part 5 additionally has a head part 6 which a cutting element 9, of tubular design, cutting with its end face 12, guides on the inside. The cutting element 9 cuts a body 13 of sleeve-shaped design out of the board 1 exactly concentrically to the guide opening 4a. With this separation procedure, the material of the body 13 is neither deformed nor compressed. The body firstly remains on the guide part 5. The guide part is removed and connected without jolting to a slideway 14. Then the body 13 is pushed onto the slideway 14 and the guide part 5 is separated. The body 13 carried by the slideway 14 is introduced, together with the latter, into a measurement device 15 of coaxial design, in which, inter alia, the permeability and the dielectricity constant of the sample body are determined.

The material of the board 1 is comparatively soft and is deformed under comparatively low mechanical stress. When taking a sample body, care must be taken, however, that the material of the body 13 is not falsified in respect of density and shape. The cutting element 9 will therefore act on the board 1 very advantageously at a comparatively slow and constant rate of forward feed, such that no mechanical deformations of the material arise. It was shown that rates of forward feed in the range of 5 mm per second to 0.1 mm per second are favorable. In particular a rate of forward feed of 1 mm per second proved to be advantageous.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for manufacturing a cylindrical body from a comparatively easily deformable material, in particular absorbents, wherein
   a plane-parallel board is firstly cut out of the material,
   a guide opening, is then introduced into and passed through this plane-parallel board, perpendicular to the surface,
   a matching guide part is inserted into the guide opening
   a tubular cutting element, guided by the guide part cuts the body out of the board, concentrically to the guide opening,
   the guide part is connected without jolting to a slideway,
   then the guide part is taken out of the body and at the same time the slideway is pulled into the body, and
   after the separation of the guide part and the slideway, the body carried by the slideway is introduced into a measurement device.

2. A process as claimed in claim 1, wherein the cutting element penetrates the board at a constant rate of forward feed in the range of 5 mm per second to 0.1 mm per second.

3. A device for carrying out the process as claimed in claim 1, having a boring machine and a support for a plane-parallel board made of comparatively easily deformable material, wherein
   it has a guide part of cylindrical design with a shaft and a head part,
   the head part is enclosed concentrically to the shaft by a cutting element, of tubular design, in effective connection with the boring machine,
   the shaft positions the plane-parallel board and penetrates this board and the support and
   the end face of the cutting element is designed as a cutting surface.

4. A device as claimed in claim 3, wherein the guide part is formed out of metal.

5. A device as claimed in claim 3, wherein at least one part of the guide part is formed out of plastic, in particular polytetrafluoroethylene.

6. A device as claimed in claim 3, wherein
   the cutting element is formed out of hardened steel and
   cutting teeth on the end face of he cutting element are ground in such a way that recorded particles of material are removed in the radial direction.

7. A device as claimed in claim 3, wherein the boring machine has adjustable rates of forward feed at least in the range of 5 mm per second to 0.1 mm per second.

8. A device as claimed in claim 3, wherein the support is provided with an intermediate layer.

* * * * *